(12) United States Patent
McPherson

(10) Patent No.: US 7,736,359 B2
(45) Date of Patent: Jun. 15, 2010

(54) RF RETURN PAD CURRENT DETECTION SYSTEM

(75) Inventor: James W. McPherson, Boulder, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 1008 days.

(21) Appl. No.: 11/331,303

(22) Filed: Jan. 12, 2006

(65) Prior Publication Data

US 2007/0161979 A1  Jul. 12, 2007

(51) Int. Cl.
*A61B 18/16* (2006.01)

(52) U.S. Cl. ...................................................... 606/35
(58) Field of Classification Search .................. 606/33, 606/34, 35, 42
See application file for complete search history.

(56) References Cited

U.S. PATENT DOCUMENTS

| | | | |
|---|---|---|---|
| 2,536,271 A | 1/1951 | Fransen et al. | |
| 3,380,445 A | 4/1968 | Frasier | |
| 3,534,306 A | 10/1970 | Watrous et al. | |
| 3,543,760 A | 12/1970 | Bolduc | |
| 3,642,008 A | 2/1972 | Bolduc | |
| 3,683,923 A | 8/1972 | Anderson | |
| 3,812,861 A | 5/1974 | Peters | |
| 3,913,583 A | 10/1975 | Bross | |
| 3,923,063 A | 12/1975 | Andrews et al. | |
| 3,933,157 A | 1/1976 | Bjurwill et al. | |
| 3,987,796 A | 10/1976 | Gonser | |
| 4,067,342 A | 1/1978 | Burton | |
| 4,092,985 A | 6/1978 | Kaufman | |
| 4,094,320 A | 6/1978 | Newton et al. | |
| 4,102,341 A | 7/1978 | Ikuno et al. | |
| 4,114,622 A | 9/1978 | Gonser | |
| 4,117,846 A | 10/1978 | Williams | |
| 4,121,590 A | 10/1978 | Gonser | |
| 4,126,137 A * | 11/1978 | Archibald | 606/38 |
| 4,166,465 A | 9/1979 | Esty et al. | |
| 4,188,927 A | 2/1980 | Harris | |
| 4,200,104 A | 4/1980 | Harris | |
| 4,200,105 A | 4/1980 | Gonser | |
| 4,213,463 A | 7/1980 | Osenkarski | |
| 4,231,372 A | 11/1980 | Newton | |

(Continued)

FOREIGN PATENT DOCUMENTS

CA   1219642   5/1987

(Continued)

OTHER PUBLICATIONS

International Search Report PCT/US2004/004196 dated Oct. 4, 2007.

(Continued)

*Primary Examiner*—Lee S Cohen

(57) ABSTRACT

The present disclosure provides an electrosurgical return pad current detection system for use in monopolar surgery as well as a method of using the same. The detection system comprises a plurality of conductive pads which include a plurality of conductive elements. The detection system further includes a sensor which senses the current returning to each conductive pad as well as a comparator which determines the difference in current among a plurality of conductive pads. If the current differential is above or below a prescribed limit, the system will alert the user of potential hazards and/or alter the amount of energy delivered to a surgical device.

21 Claims, 4 Drawing Sheets

U.S. PATENT DOCUMENTS

| | | | |
|---|---|---|---|
| 4,237,887 A | 12/1980 | Gonser |
| 4,253,721 A | 3/1981 | Kaufman |
| 4,303,073 A | 12/1981 | Archibald |
| 4,304,235 A | 12/1981 | Kaufman |
| 4,331,149 A | 5/1982 | Gonser |
| 4,343,308 A | 8/1982 | Gross |
| 4,381,789 A | 5/1983 | Naser et al. |
| 4,384,582 A | 5/1983 | Watt |
| 4,387,714 A | 6/1983 | Geddes et al. |
| 4,393,584 A | 7/1983 | Bare et al. |
| 4,416,276 A | 11/1983 | Newton et al. |
| 4,416,277 A | 11/1983 | Newton et al. |
| 4,437,464 A | 3/1984 | Crow |
| 4,494,541 A | 1/1985 | Archibald |
| 4,643,193 A | 2/1987 | DeMarzo |
| 4,657,015 A | 4/1987 | Irnich |
| 4,658,819 A | 4/1987 | Harris et al. |
| 4,662,369 A | 5/1987 | Ensslin |
| 4,669,468 A | 6/1987 | Cartmell et al. |
| 4,699,146 A | 10/1987 | Sieverding |
| 4,722,761 A | 2/1988 | Cartmell et al. |
| 4,725,713 A | 2/1988 | Lehrke |
| 4,741,334 A | 5/1988 | Irnich |
| 4,745,918 A | 5/1988 | Feucht |
| 4,748,983 A | 6/1988 | Shigeta et al. |
| 4,750,482 A | 6/1988 | Sieverding |
| 4,754,757 A | 7/1988 | Feucht |
| 4,768,514 A | 9/1988 | DeMarzo |
| 4,770,173 A | 9/1988 | Feucht et al. |
| 4,788,977 A | 12/1988 | Farin et al. |
| 4,799,480 A | 1/1989 | Abraham et al. |
| 4,807,621 A | 2/1989 | Hagen et al. |
| 4,844,063 A | 7/1989 | Clark |
| 4,848,335 A | 7/1989 | Manes |
| 4,862,889 A | 9/1989 | Feucht |
| 4,873,974 A | 10/1989 | Hagen et al. |
| 4,895,169 A | 1/1990 | Heath |
| 4,942,313 A | 7/1990 | Kinzel |
| 4,947,846 A | 8/1990 | Kitagawa et al. |
| 4,955,381 A | 9/1990 | Way et al. |
| 4,961,047 A | 10/1990 | Carder |
| 4,969,885 A | 11/1990 | Farin |
| 5,000,753 A | 3/1991 | Hagen et al. |
| 5,004,425 A | 4/1991 | Hee |
| 5,010,896 A | 4/1991 | Westbrook |
| 5,038,796 A | 8/1991 | Axelgaard et al. |
| 5,042,981 A | 8/1991 | Gross |
| 5,061,914 A | 10/1991 | Busch et al. |
| 5,087,257 A | 2/1992 | Farin |
| 5,114,424 A | 5/1992 | Hagen et al. |
| 5,152,762 A | 10/1992 | McElhenney |
| 5,160,334 A | 11/1992 | Billings et al. |
| 5,196,008 A | 3/1993 | Kuenecke et al. |
| 5,246,439 A | 9/1993 | Hebborn et al. |
| 5,271,417 A | 12/1993 | Swanson et al. |
| 5,276,079 A | 1/1994 | Duan et al. |
| 5,286,255 A | 2/1994 | Weber |
| 5,312,401 A | 5/1994 | Newton et al. |
| 5,336,255 A | 8/1994 | Kanare et al. |
| 5,352,315 A | 10/1994 | Carrier et al. |
| 5,362,420 A | 11/1994 | Itoh et al. |
| 5,370,645 A | 12/1994 | Klicek et al. |
| 5,385,679 A | 1/1995 | Uy et al. |
| 5,388,490 A | 2/1995 | Buck |
| 5,389,376 A | 2/1995 | Duan et al. |
| 5,390,382 A | 2/1995 | Hannant et al. |
| 5,409,966 A | 4/1995 | Duan et al. |
| 5,447,513 A | 9/1995 | Davison et al. |
| 5,449,365 A | 9/1995 | Green et al. |
| 5,452,725 A | 9/1995 | Martenson |
| 5,480,399 A | 1/1996 | Hebborn |
| 5,496,312 A | 3/1996 | Klicek |
| 5,496,363 A | 3/1996 | Burgio et al. |
| 5,520,180 A | 5/1996 | Uy et al. |
| 5,536,446 A | 7/1996 | Uy et al. |
| 5,540,684 A | 7/1996 | Hassler, Jr. |
| 5,599,347 A * | 2/1997 | Hart et al. ............... 606/42 |
| 5,601,618 A | 2/1997 | James |
| 5,611,709 A | 3/1997 | McAnulty |
| 5,632,280 A | 5/1997 | Leyde et al. |
| 5,643,319 A | 7/1997 | Green et al. |
| 5,660,892 A | 8/1997 | Robbins et al. |
| 5,670,557 A | 9/1997 | Dietz et al. |
| 5,674,561 A | 10/1997 | Dietz et al. |
| 5,678,545 A | 10/1997 | Stratbucker |
| 5,688,269 A | 11/1997 | Newton et al. |
| 5,695,494 A | 12/1997 | Becker |
| 5,707,369 A | 1/1998 | Vaitekunas et al. |
| 5,718,719 A | 2/1998 | Clare et al. |
| 5,720,744 A | 2/1998 | Eggleston et al. |
| 5,766,165 A | 6/1998 | Gentelia et al. |
| 5,779,632 A | 7/1998 | Dietz et al. |
| 5,797,902 A | 8/1998 | Netherly |
| 5,800,426 A | 9/1998 | Taki et al. |
| 5,817,091 A | 10/1998 | Nardella et al. |
| 5,830,212 A | 11/1998 | Cartmell et al. |
| 5,836,942 A | 11/1998 | Netherly et al. |
| 5,846,558 A | 12/1998 | Nielsen et al. |
| 5,853,750 A | 12/1998 | Dietz et al. |
| 5,868,742 A | 2/1999 | Manes et al. |
| 5,924,983 A | 7/1999 | Takaki et al. |
| 5,947,961 A | 9/1999 | Netherly |
| 5,952,398 A | 9/1999 | Dietz et al. |
| 5,971,981 A | 10/1999 | Hill et al. |
| 5,976,128 A | 11/1999 | Schilling et al. |
| 5,985,990 A | 11/1999 | Kantner et al. |
| 5,999,061 A | 12/1999 | Pope et al. |
| 6,007,532 A | 12/1999 | Netherly |
| 6,010,054 A | 1/2000 | Johnson et al. |
| 6,030,381 A | 2/2000 | Jones et al. |
| 6,032,063 A | 2/2000 | Hoar et al. |
| 6,039,732 A | 3/2000 | Ichikawa et al. |
| 6,053,910 A | 4/2000 | Fleenor |
| RE36,720 E | 5/2000 | Green et al. |
| 6,059,778 A | 5/2000 | Sherman |
| 6,063,075 A | 5/2000 | Mihori |
| 6,083,221 A | 7/2000 | Fleenor et al. |
| 6,086,249 A | 7/2000 | Urich |
| 6,121,508 A | 9/2000 | Bischof et al. |
| 6,135,953 A | 10/2000 | Carim |
| 6,171,304 B1 | 1/2001 | Netherly et al. |
| 6,200,314 B1 | 3/2001 | Sherman |
| 6,203,541 B1 | 3/2001 | Keppel |
| 6,214,000 B1 | 4/2001 | Fleenor et al. |
| 6,232,366 B1 | 5/2001 | Wang et al. |
| 6,240,323 B1 | 5/2001 | Calenzo, Sr. et al. |
| 6,258,085 B1 | 7/2001 | Eggleston |
| 6,275,786 B1 | 8/2001 | Daners |
| 6,301,500 B1 | 10/2001 | Van Herk et al. |
| 6,310,611 B1 | 10/2001 | Caldwell |
| 6,347,246 B1 | 2/2002 | Perrault et al. |
| 6,350,264 B1 | 2/2002 | Hooven |
| 6,357,089 B1 | 3/2002 | Koguchi et al. |
| 6,358,245 B1 | 3/2002 | Edwards et al. |
| 6,379,161 B1 | 4/2002 | Ma |
| 6,409,722 B1 | 6/2002 | Hoey et al. |
| 6,413,255 B1 | 7/2002 | Stern |
| 6,415,170 B1 | 7/2002 | Loutis et al. |
| 6,454,764 B1 | 9/2002 | Fleenor et al. |
| 6,488,678 B2 | 12/2002 | Sherman |
| 6,537,272 B2 | 3/2003 | Christopherson et al. |
| 6,544,258 B2 | 4/2003 | Fleenor et al. |
| 6,546,270 B1 | 4/2003 | Goldin et al. |
| 6,565,559 B2 | 5/2003 | Eggleston |

| | | |
|---|---|---|
| 6,569,160 B1 | 5/2003 | Goldin et al. |
| 6,582,424 B2 | 6/2003 | Fleenor et al. |
| 6,666,859 B1 | 12/2003 | Fleenor et al. |
| 6,669,073 B2 | 12/2003 | Milliman et al. |
| 6,736,810 B2 | 5/2004 | Hoey et al. |
| 6,796,828 B2 | 9/2004 | Ehr et al. |
| 6,799,063 B2 | 9/2004 | Carson |
| 6,830,569 B2 | 12/2004 | Thompson et al. |
| 6,849,073 B2 | 2/2005 | Hoey et al. |
| 6,860,881 B2 | 3/2005 | Sturm |
| 6,875,210 B2 | 4/2005 | Reflio et al. |
| 6,892,086 B2 | 5/2005 | Russell |
| 6,905,497 B2 | 6/2005 | Truckai et al. |
| 6,939,344 B2 | 9/2005 | Kreindel |
| 6,948,503 B2 | 9/2005 | Refior et al. |
| 6,953,139 B2 | 10/2005 | Milliman et al. |
| 6,959,852 B2 | 11/2005 | Shelton, IV et al. |
| 6,997,735 B2 | 2/2006 | Ehr et al. |
| 7,025,765 B2 | 4/2006 | Balbierz et al. |
| 7,128,253 B2 | 10/2006 | Mastri et al. |
| 7,143,926 B2 | 12/2006 | Shelton, IV et al. |
| 7,160,293 B2 | 1/2007 | Sturm et al. |
| 7,166,102 B2 | 1/2007 | Fleenor et al. |
| 7,169,144 B2 | 1/2007 | Hoey et al. |
| 7,169,145 B2 | 1/2007 | Isaacson et al. |
| 7,182,604 B2 | 2/2007 | Ehr et al. |
| 7,220,260 B2 | 5/2007 | Fleming et al. |
| 7,229,307 B2 | 6/2007 | Ehr et al. |
| 7,258,262 B2 | 8/2007 | Mastri et al. |
| 7,267,675 B2 | 9/2007 | Stern et al. |
| 7,278,562 B2 | 10/2007 | Mastri et al. |
| 7,303,107 B2 | 12/2007 | Milliman et al. |
| 7,308,998 B2 | 12/2007 | Mastri et al. |
| 7,311,560 B2 | 12/2007 | Ehr et al. |
| 7,357,287 B2 | 4/2008 | Shelton, IV et al. |
| 7,380,695 B2 | 6/2008 | Doll et al. |
| 7,422,589 B2 | 9/2008 | Newton et al. |
| 7,473,145 B2 | 1/2009 | Ehr et al. |
| 2003/0139741 A1 | 7/2003 | Goble et al. |
| 2004/0150504 A1 | 8/2004 | Nicholson |
| 2005/0021022 A1 | 1/2005 | Sturm et al. |
| 2005/0079752 A1 | 4/2005 | Ehr et al. |
| 2005/0085806 A1 | 4/2005 | Auge, II et al. |
| 2005/0101947 A1 | 5/2005 | Jarrard et al. |
| 2005/0251130 A1 | 11/2005 | Boveja et al. |
| 2006/0030195 A1 | 2/2006 | Ehr et al. |
| 2006/0041251 A1 | 2/2006 | Odell et al. |
| 2006/0041252 A1 | 2/2006 | Odell et al. |
| 2006/0041253 A1 | 2/2006 | Newton et al. |
| 2006/0074411 A1 | 4/2006 | Carmel et al. |
| 2006/0079872 A1 | 4/2006 | Eggleston |
| 2006/0173250 A1 | 8/2006 | Nessler |
| 2006/0217742 A1 | 9/2006 | Messerly et al. |
| 2006/0224150 A1 | 10/2006 | Arts et al. |
| 2007/0049914 A1 | 3/2007 | Eggleston |
| 2007/0049916 A1 | 3/2007 | Isaacson et al. |
| 2007/0049919 A1 | 3/2007 | Lee, Jr. et al. |
| 2007/0073284 A1 | 3/2007 | Sturm |
| 2007/0074719 A1 | 4/2007 | Danek et al. |
| 2007/0161979 A1 | 7/2007 | McPherson |
| 2007/0167942 A1 | 7/2007 | Rick |
| 2007/0203481 A1 | 8/2007 | Gregg et al. |
| 2007/0244478 A1 | 10/2007 | Bahney |
| 2008/0009846 A1 | 1/2008 | Ward |
| 2008/0033276 A1 | 2/2008 | Ehr et al. |
| 2008/0083806 A1 | 4/2008 | Scirica |
| 2008/0083813 A1 | 4/2008 | Zemlok et al. |
| 2008/0249520 A1 | 10/2008 | Dunning et al. |
| 2008/0249524 A1 | 10/2008 | Dunning |
| 2008/0281309 A1 | 11/2008 | Dunning et al. |
| 2008/0281310 A1 | 11/2008 | Dunning et al. |
| 2008/0281311 A1 | 11/2008 | Dunning et al. |
| 2009/0036884 A1 | 2/2009 | Gregg et al. |
| 2009/0036885 A1 | 2/2009 | Gregg |

FOREIGN PATENT DOCUMENTS

| | | |
|---|---|---|
| DE | 3206947 | 9/1983 |
| DE | 3544443 | 6/1987 |
| DE | 42 38 263 A1 | 5/1993 |
| DE | 4231236 | 3/1994 |
| DE | 197 17 411 A1 | 11/1998 |
| DE | 198 01 173 | 7/1999 |
| DE | 103 28 514 | 6/2003 |
| DE | 102004010940 | 9/2005 |
| EP | 0262888 | 4/1988 |
| EP | 390937 | 10/1990 |
| EP | 836868 | 4/1998 |
| EP | 0 930 048 | 7/1999 |
| EP | 1 051 949 A1 | 11/2000 |
| EP | 1076350 | 2/2001 |
| EP | 1 468 653 | 10/2004 |
| EP | 1 645 236 | 4/2006 |
| EP | 1707151 | 10/2006 |
| EP | 1 808 144 | 7/2007 |
| EP | 1902684 | 3/2008 |
| FR | 2276027 | 6/1974 |
| FR | 2516782 | 5/1983 |
| GB | 2 054 382 | 2/1981 |
| GB | 2374532 | 10/2002 |
| WO | WO 96/19152 | 6/1996 |
| WO | WO 97/37719 | 10/1997 |
| WO | WO 98/18395 | 5/1998 |
| WO | WO 98/53751 | 12/1998 |
| WO | WO 99/09899 | 3/1999 |
| WO | WO 99/11187 | 3/1999 |
| WO | WO 00/06246 | 2/2000 |
| WO | WO 00/32122 | 6/2000 |
| WO | WO 00/53113 | 9/2000 |
| WO | WO 00/65993 | 11/2000 |
| WO | WO 01/87175 A1 | 11/2001 |
| WO | WO 02/058579 A1 | 8/2002 |
| WO | WO 02/060526 A1 | 8/2002 |
| WO | WO 02/099442 | 12/2002 |
| WO | WO 03/094766 | 11/2003 |
| WO | WO 2004/028385 | 4/2004 |
| WO | WO 2004/074854 | 9/2004 |
| WO | WO 2005/048809 | 6/2005 |
| WO | WO 2005/087124 | 9/2005 |
| WO | WO 2005/099606 | 10/2005 |
| WO | WO 2005/110263 | 11/2005 |
| WO | WO 2005/115262 | 12/2005 |
| WO | WO 2008/009385 | 1/2008 |

OTHER PUBLICATIONS

International Search Report EP06006961.4 dated Oct. 5, 2007.
International Search Report EP07000885.9 dated May 2, 2007.
International Search Report EP07007783.9 dated Aug. 6, 2007.
International Search Report EP06018206.0 dated Oct. 13, 2006.
International Search Report EP 05021944.3 dated Jan. 25, 2006.
International Search Report EP 05002027.0 dated May 12, 2005.
International Search Report from EP 06006961 dated Aug. 3, 2006.
Boyles, Walt; "Instrumentation Reference Book", 2002; Butterworth-Heinemann ; 262-264.
International Search Report EP06023756.7 dated Feb. 21, 2008.
International Search Report EP07018375.1 dated Jan. 8, 2008.
International Search Report EP07019173.9 dated Feb. 12, 2008.
International Search Report EP07019178.8 dated Feb. 12, 2008.
International Search Report EP07253835.8 dated Feb. 20, 2007.
International Search Report EP08006731.7 dated Jul. 29, 2008.
International Search Report EP08006734.1 dated Aug. 18, 2008.
International Search Report EP07000567.3 dated Dec. 3, 2008.
International Search Report EP08006731 dated Jul. 14, 2008.
International Search Report EP08006735.8 dated Jan. 8, 2009.
International Search Report EP08008510.3 dated Oct. 27, 2008.
International Search Report EP08013758.1 dated Nov. 20, 2008.

International Search Report EP08013760.7 dated Nov. 20, 2008.
International Search Report EP08155779—partial dated Sep. 8, 2008.
International Search Report EP08155779 dated Jan. 23, 2009.
International Search Report EP09152032 dated Jun. 17, 2009.
International Search Report EP09152130.2 dated Apr. 6, 2009.

* cited by examiner

RF RETURN PAD CURRENT DETECTION SYSTEM

BACKGROUND

1. Technical Field

The present disclosure is directed to an electrosurgical apparatus and method, and, is particularly directed to a patient return electrode pad and a method for performing monopolar surgery and RF ablation using the same.

2. Background

During electrosurgery, a source or active electrode delivers energy, such as radio frequency energy, from an electrosurgical generator to a patient. A return electrode carries the current back to the electrosurgical generator. In monopolar electrosurgery, the source electrode is typically a hand-held instrument placed by the surgeon at the surgical site and the high current density flow at this electrode creates the desired surgical effect of cutting, ablating and/or coagulating tissue. The patient return electrode is placed at a remote site from the source electrode and is typically in the form of a pad adhesively adhered to the patient.

The return electrode typically has a relatively large patient contact surface area to minimize heat concentrations at that patient pad site (i.e., the smaller the surface area, the greater the current density and the greater the intensity of the heat.) Hence, the overall area of the return electrode that is adhered to the patient is generally important because it minimizes the chances of current concentrating in any one spot which may cause patient burns. A larger surface contact area is desirable to reduce heat intensity. The size of return electrodes is based on assumptions of the anticipated maximum current during a particular surgical procedure and the duty cycle (i.e., the percentage of time the generator is on) during the procedure. The first types of return electrodes were in the form of large metal plates covered with conductive jelly. Later, adhesive electrodes were developed with a single metal foil covered with conductive jelly or conductive adhesive. However, one problem with these adhesive electrodes was that if a portion peeled from the patient, the contact area of the electrode with the patient decreased, thereby increasing the current density at the adhered portion and, in turn, increasing the heat applied to the tissue. This risked burning the patient in the area under the adhered portion of the return electrode if the tissue was heated beyond the point where normal circulation of blood could cool the skin.

To address this problem, split return electrodes and hardware circuits, generically called Return Electrode Contact Quality Monitors (RECQMs), were developed. These split electrodes consist of two separate conductive foils arranged as two halves of a single return electrode. The hardware circuit uses an AC signal between the two electrode halves to measure the impedance therebetween. This impedance measurement is indicative of how well the return electrode is adhered to the patient since the impedance between the two halves is directly related to the area of patient contact. That is, if the electrode begins to peel from the patient, the impedance increases since the contact area of the electrode decreases. Current RECQMs are designed to sense this change in impedance so that when the percentage increase in impedance exceeds a predetermined value or the measured impedance exceeds a threshold level, the electrosurgical generator is shut down to reduce the chances of burning the patient.

As new surgical and therapeutic RF procedures continue to be developed that utilize higher current and higher duty cycles, increased heating of tissue under the return electrode may occur. Ideally, each conductive pad would receive substantially the same amount of current, therefore reducing the possibility of a pad site burn. However, this is not always possible due to patient size, incorrect placement of pads, differing tissue consistencies, etc. It would therefore be advantageous to design a return electrode pad which has the ability to detect and correct a current imbalance between pads, therefore reducing the likelihood of patient burns.

SUMMARY

The present disclosure provides an electrosurgical return pad current detection system for use in monopolar surgery. The detection system comprises a plurality of conductive pads which include a plurality of conductive elements. The detection system further includes a plurality of sensors which sense the current returning to each conductive pad as well as a comparator for sensing the difference in current between a plurality of conductive pads.

The present disclosure may also include an ablation generator which may regulate the amount of power delivered to a surgical device. In operation, the return pad current detection system is placed in contact with the patient. A generator enables the transfer of radio frequency current from an active electrode to at least one of a plurality of conductive elements. The plurality of sensors measures the amount of current returning to each pad. This information in then processed a comparator which detects any possible imbalances in current between the pads. If there is a substantial imbalance the user is warned of such a situation and the generator automatically corrects the imbalances.

In one embodiment of the present disclosure the current sensor of each conductive pad is a current sense transformer. Alternatively, the current sensor could be, inter alia, a non-inductive sense resistor.

In another embodiment of the present disclosure the comparator is a differential or instrumentation amplifier.

It is envisioned for the generator to utilize the information provided by the comparator to alert the user of potential hazardous conditions and to prevent injury. This may be achieved using a variety of differing methods including safety control, neural network, or fuzzy logic algorithms.

In one embodiment, a full-wave rectifier is connected to the current sensor in order to convert the returning current signal from alternating current to direct current.

The present disclosure also includes a method for performing monopolar surgery. The method utilizes the return pad current detection system as described above. The method also includes placing the return pad current detection system in contact with a patient; generating electrosurgical energy via an electrosurgical generator; supplying the electrosurgical energy to the patient via an active electrode; measuring the current returning to each conductive pad; detecting imbalances in current by comparing the current returning to one conductive pad with the current returning to each of the remaining pads; warning the user of possible hazardous conditions; and substantially correcting or regulating the imbalances among pads.

For a better understanding of the present disclosure and to show how it may be carried into effect, reference will now be made by way of example to the accompanying drawings.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
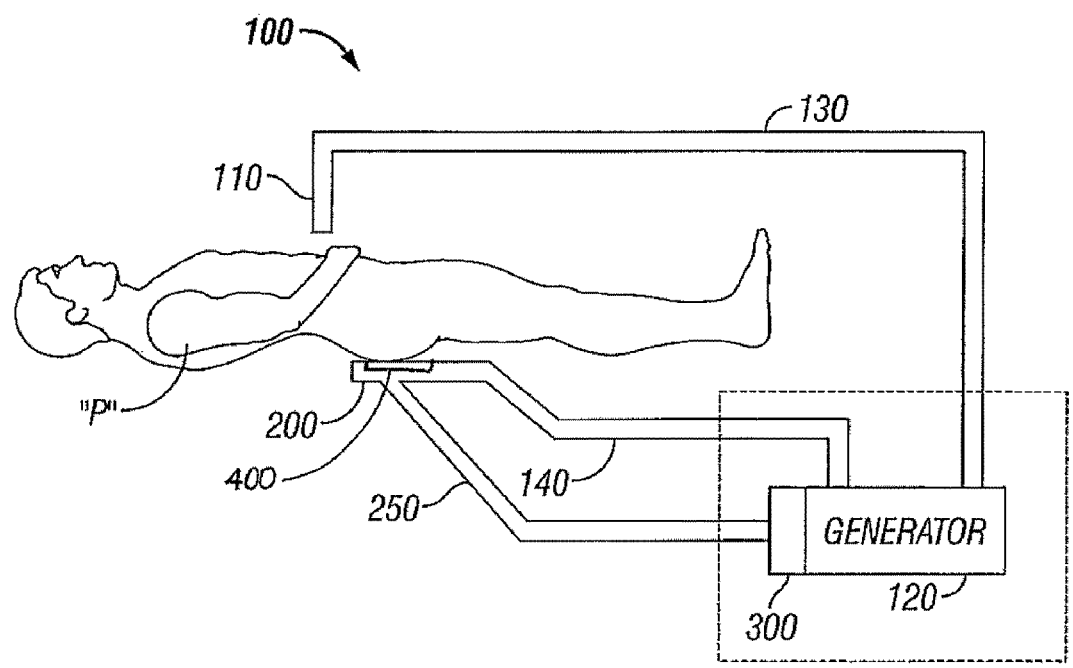
FIG. 1 is a schematic illustration of a monopolar electrosurgical system.

Embodiments of the presently disclosed multiple RF return pad current detection system and method of using the same are described herein with reference to the accompanying drawing figures wherein like reference numerals identify similar or identical elements. In the following description, well-known functions or constructions are not described in detail to avoid obscuring the disclosure in unnecessary detail.

Figure 4:
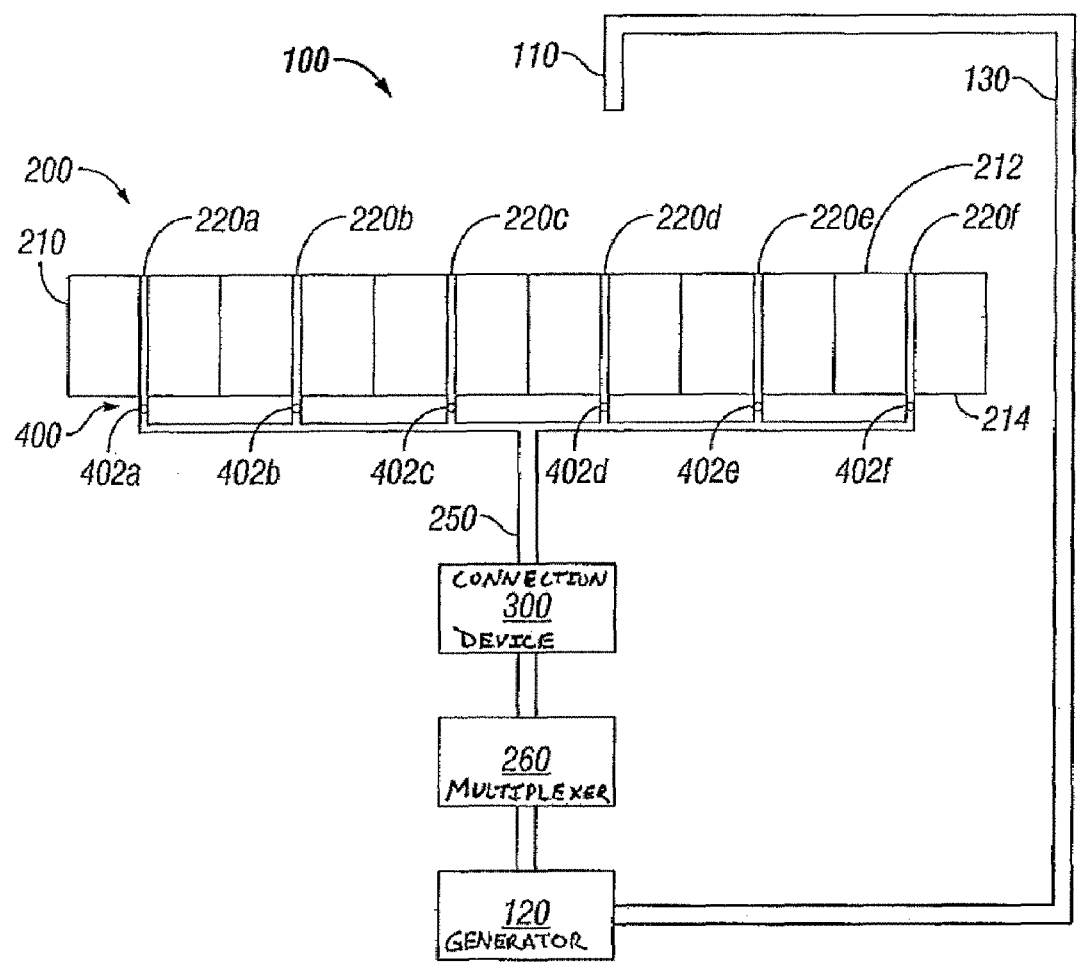
FIG. 4 is an enlarged schematic cross-sectional view of a portion of the return electrodes.

Referring initially to FIG. 1, a schematic illustration of a monopolar electrosurgical system 100 is shown. The electrosurgical system 100 generally includes a surgical instrument (e.g., electrosurgical pencil, electrical scalpel, or other active electrode) 110, a return electrode 200, a connection device 300 for connecting the return electrode 200 to a generator 120, and a current detection system 400 disposed on or operatively associated with the return electrode 200 (FIG. 4). In FIG. 1, the return electrode 200 is illustrated placed under a patient "P." Electrosurgical energy is supplied to the surgical instrument 110 by the generator 120 via a cable 130 to cut, coagulate, blend, etc. tissue. The return electrode 200 returns energy delivered by the surgical instrument 110 to the patient "P" back to the generator 120 via return path 140.

The current detection system 400 is in operative engagement with the return electrode 200 and operatively connected to the connection device 300 via a cable 250. The connection device 300 may be operatively connected to the generator 120 (FIG. 1), may be operatively connected to the return electrode 200 (FIGS. 2 and 3), may be disposed between the return electrode 200 and a generator 120 (FIG. 4) or housed within generator 120.

Figure 2:
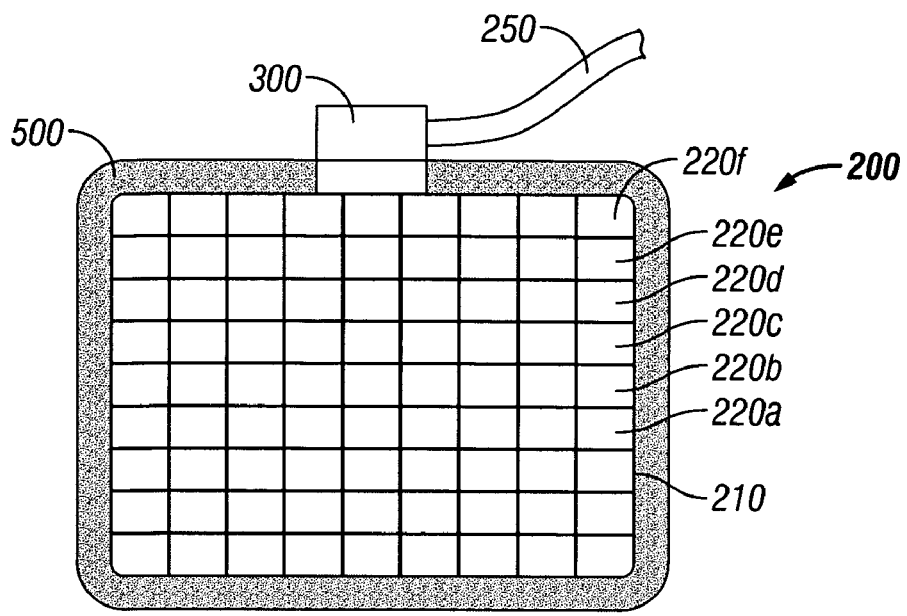
FIG. 2 is a plan view of an electrosurgical return electrode according to one embodiment of the present disclosure, illustrating a conductive pad having a grid of conductive elements of substantially equal sizes.
Figure 3:
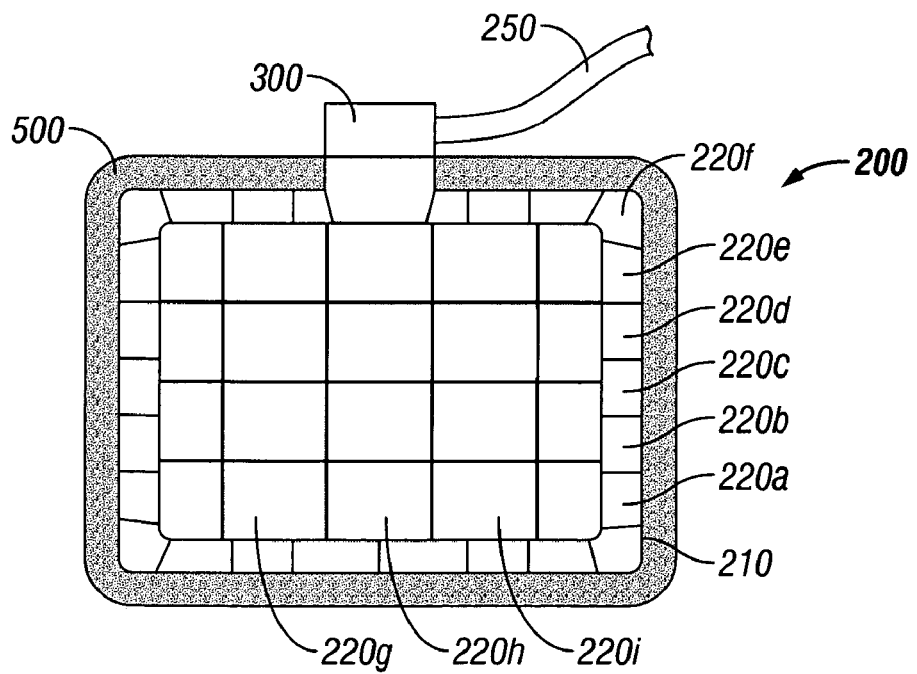
FIG. 3 is a plan view of an electrosurgical return electrode according to another embodiment of the present disclosure, illustrating a conductive pad having a grid of conductive elements of varying sizes.

FIGS. 2, 3 and 4 illustrate various embodiments of the return electrode 200 for use in monopolar electrosurgery. Generally, the return electrode 200 is a conductive pad 210 having a top surface 212 (FIG. 4) and a bottom surface 214 (FIG. 4). The return electrode 200 is designed and configured to receive current during monopolar electrosurgery. While the figures depict the return electrode 200 in a general rectangular shape, it is within the scope of the disclosure for the return electrode 200 to have any regular or irregular shape, such as circular, polygonal, etc.

As illustrated in FIGS. 2, 3 and 4, the conductive pad 210 is comprised of a plurality of conductive elements (only conductive elements 220a-220f are labeled for clarity) arranged in a regular or irregular array. Each of the plurality of conductive elements 220 may be equally-sized or differently-sized and may form a grid/array (or be disposed in any other grid-like arrangement) on the conductive pad 210. It is also envisioned and within the scope of the present disclosure for the plurality of conductive elements 220a-220f to be arranged in a spiral or radial orientation (not shown) on the conductive pad 210.

Figure 5:
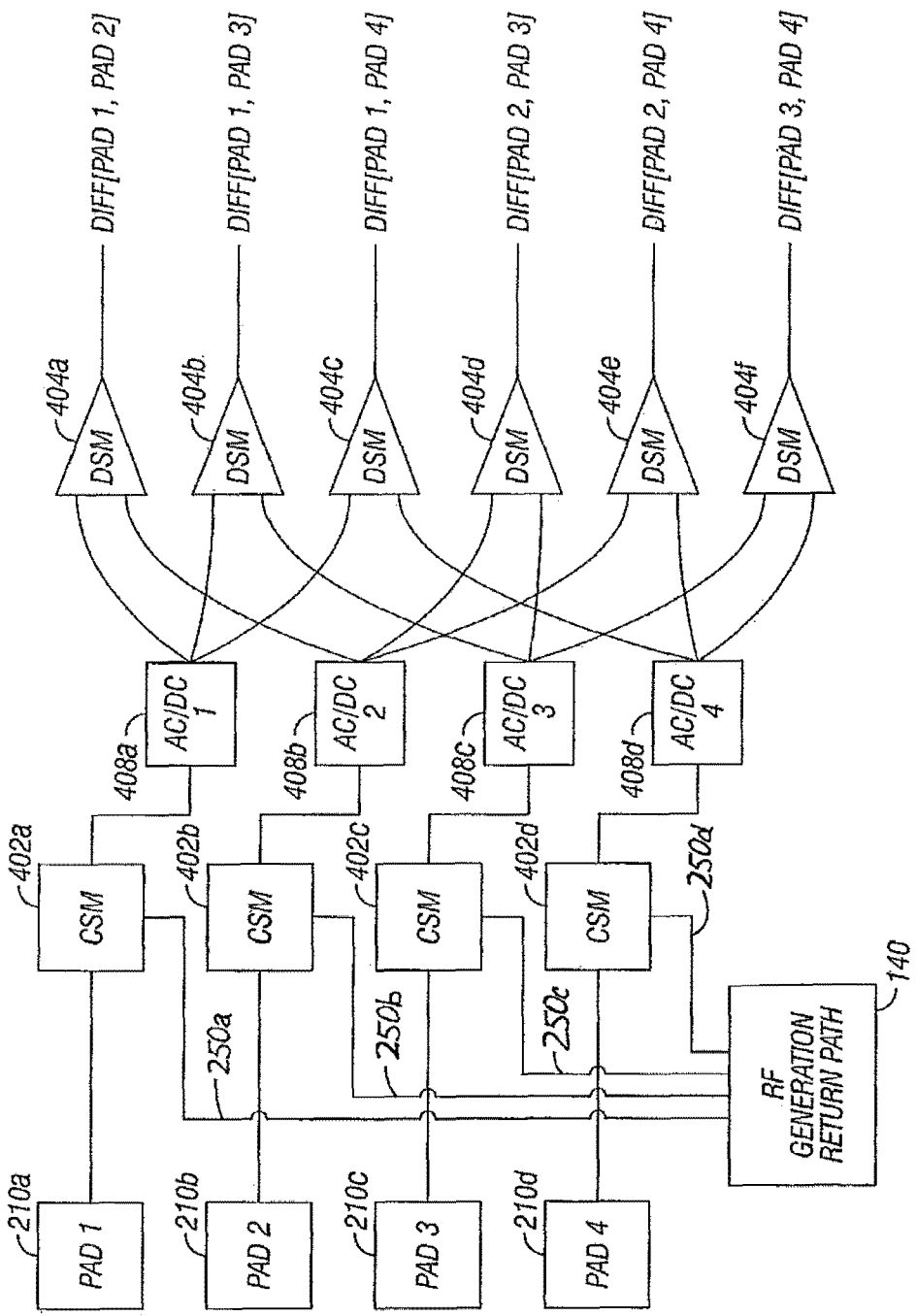
FIG. 5 is an electrical schematic of the multiple RF return pad current detection system.

As illustrated in FIG. 4, current detection system 400 includes an array of individual current sensors (illustrated as 402a-402f, corresponding to conductive elements 220a-220f, respectively), which are able to measure the amount of current returning to each pad, e.g., 210a. The current detection system 400 may be operatively connected to the plurality of conductive elements 220a-f on the top surface 212 or bottom surface 214 (or anywhere therebetween) of conductive pad 210. For example, individual current sensors 402a may be operatively connected to conductive element 220a. Moreover, each current sensor, e.g. 402a may be connected via a common cable 250 to a comparator 404 (see FIG. 5), which may be housed in a multitude of different configurations, including within connection device 300 or generator 120. Alternatively, a series of current detection systems, e.g. 402a, maybe connected to a connection device 300 via a respective cable 250a (FIG. 5). In the interest of clarity, each of the possible cable arrangements for cables 250a-d connected to each current detection system 402a-d are not illustrated.

Generally, the area of the return electrode 200 that is in contact with the patient "P" affects the current density of a signal that heats the patient "P." The smaller the contact area the return electrode pad 210 has with the patient "P," the greater the current density which directly affects tissue heating at the contact site. Conversely, the greater the contact area of the return electrode 200, the smaller the current density and the less heating of tissue at the patient site. As can be appreciated, higher current densities lead to greater heating of tissue and greater probability of patient burn. It is therefore important to either ensure a relatively high amount of contact area between the return electrode pad 210 and the patient "P," or otherwise maintain a relatively low current density on the return electrode pad 210.

While there are various methods of maintaining a relatively low current density (including, inter alia, the use of electrosurgical return electrode monitors (REMs), such as the one described in commonly-owned U.S. Pat. No. 6,565,559, the entire contents of which are hereby incorporated by reference herein), the present disclosure ensures low current density at the patient site by sensing the amount of current returning to each of the plurality of conductive elements 220a-f of the return electrode 200 and adjusting the energy accordingly to reduce current densities at the patient site.

More particularly, the current detection system 400 of the present disclosure has the ability to measure the amount of current returning to each conductive element 220a-220f. Each conductive element 220a-f is connected to the connection device 300 and may be activated and/or deactivated (or adjusted) as needed. For example, if a conductive element (e.g., 220a) along the perimeter of the conductive pad 210 becomes relatively hot, that conductive element 220a may be disconnected from the connection device 300, deactivated or adjusted to receive a lower amount of energy. In this example, the conductive element 220a would not receive any more energy or receive a reduced amount of energy and the current level in the area of the pad contacting the conductive element 220a would dissipate. It is envisioned and within the scope of the present disclosure for the disconnection/re-connection, deactivation/reactivation of the conductive elements 220a-f to occur automatically as a result of an algorithm (or the like) provided in the electrosurgical generator 120.

It is also envisioned and within the scope of the present disclosure for a disconnected conductive element, e.g., 220a, to be reconnected to the connection device 300 when the current level of a particular conductive element or particular area of the pad 210 in contact with the corresponding current detection system 400 decreases. Utilizing these features, the current levels of the return electrode 200 can be relatively consistent throughout the entire surface thereof, thus reducing the possibility of "hot spots" and patient burns. For example, the grid-like arrangement of the pad 210 makes it easier for the generator 120 to identify and adjust current levels at different pad 210 locations depending upon the current build-up possibly reducing the likelihood of patient burns.

Referring now to FIG. 5, the current detection systems 400 may be operatively associated with a plurality of pads 210a-d which operatively connect to generator 140. One or more algorithms controls the electrical energy associated with each pad to reduce patient burn. Current detection system 400 includes a sensing device 402a for sensing the current to each conductive pad 210a-210d as well as at least one a comparator 404a-404f which senses the difference in current between the plurality of conductive pads 210a-210d. Current detection system 400 is connected to a plurality of conductive elements 220a-220f (see FIGS. 2 and 3) on each pad 210a-210d and may be located in a variety of different areas including, on conductive pads 210a-210d, inside connection device 300, or within generator 120. Other locations for current detection system 400 are envisioned and are within the scope of the present disclosure.

The current sensor(s), e.g., 402a may take a number of different forms including, but not limited to, open loop sensors, closed loop sensors, digital current sensors, Hall-effect devices or a current sense transformer (not shown), the operation of which will be described hereinbelow. In use, the return current for each conductive pad e.g., 210a, is passed through a toroidal magnetic, which forms a 1:N current sense transformer comprised of 1 turn from the return wire and N turns of the toroidal core. The waveform representing the current can be converted to a voltage waveform by placing a resistor between the terminations of the toroidal core turns. This voltage waveform is substantially sinusoidal in nature and may require further modification. An AC/DC converter circuit, e.g. 408a, may be utilized to substantially convert the alternating current signal of the return current into a direct current signal. This eliminates any phase or frequency modulation that could lead to inaccuracies in measurement. This DC response is representative of the amount of RF current flowing through each conductive pad 210. AC/DC converter circuit may be operatively associated with each respective sensor 402a-402d.

Once the DC response of each conductive pad 210a is obtained, the signal may then be fed into a comparator e.g., 404a. Each comparator 404a receives two distinct DC inputs, each from a separate conductive pad, e.g., 210a, 210b. It is envisioned that one possible type of comparator 404a is an instrumentation amplifier. Instrumentation amplifier receives a DC input from two different conductive pads 210a, 210b and calculates the current differential between the two. This difference is then multiplied by the gain of comparator or instrumentation amplifier 404a in order to obtain a scaled representation of imbalances between any two of the pads e.g. 210a, 210b. Ideally, the current differential would be negligible with each pad receiving the same amount of return current. However, if a substantial imbalance is present, a warning is provided via a warning device (audible or visual) or safety control algorithms which are utilized to mitigate pad site burns which will be described hereinbelow.

Generator 120 may contain, inter alia, embedded software. It is envisioned that this embedded software may be utilized to develop safety control algorithms or similar warning mechanisms. Using the information provided by comparator(s) 404a-404d, generator 120 may be able to modulate the amount of power delivered to each conductive pad 210a-210d therefore minimizing the chances of pad site burns. Moreover, this information may also be processed using a variety of different techniques, including but not limited to, neural networks or fuzzy logic algorithms.

It should be noted that a current sense transformer may be replaced with any current measuring device such as a non-inductive sense resistor. Similarly, comparator or instrumentation amplifier could be replaced with a number of different devices including, but not limited to, differential amplifiers. Moreover, AC/DC converter circuit(s) 408a-408d may take on a number of different forms such as a full-wave rectifier circuit.

During electrosurgical use of the return electrode pad 210, portions of the perimeter of the return electrode pad 210 may become hot at a faster rate than the center of the return electrode pad 210. In such a situation, as seen in FIG. 3, it may be desirable to have the conductive elements 220a-220f near the perimeter of the return electrode pad 210 be smaller than the remaining conductive elements 220g-220i. Monitoring the returning current levels of each conductive pad(s) 210a-210d and each conductive element 220a-220i of each pad 210a-210d would allow greater control of the overall temperature of the portions of the patient "P" in contact with the entire return electrode pad or pads. Thus, the return electrode pad 210, as a whole, would be able to receive a greater amount of current, as some new procedures necessitate. Moreover, and as illustrated in FIG. 5, a plurality of pads 210a-210d may be utilized each with a plurality of conductive elements 220a-220i which all may be individually regulated or controlled to reduce patient burns.

To further limit the possibility of patient burns, it is envisioned that an adhesive layer 500 may be disposed on the return electrode 200 about the periphery of pad 210, as illustrated in FIGS. 2 and 3. The adhesive layer 500 may be conductive and may be made from materials that include, but are not limited to, a polyhesive adhesive; a Z axis adhesive; or a water-insoluble, hydrophilic, pressure-sensitive adhesive and is desirably made of a polyhesive adhesive. Such materials are described in U.S. Pat. Nos. 4,699,146 and 4,750,482, the entire contents of each of which are herein incorporated by reference. A function of the adhesive layer 500 is to ensure an optimal surface contact area between the return electrode 200 and the patient "P" thus limiting the possibility of a patient burn.

It is envisioned that the return electrode(s) 200 may be entirely disposable, entirely re-usable, or a combination thereof. In one embodiment, the conductive elements 220 are re-usable, while the adhesive layer 500 is disposable. Other combinations of disposable/re-usable portions of the return electrode 200 are envisioned and within the scope of the present disclosure.

It is envisioned that a multiplexer 260 may be employed to control switching of the plurality of conductive elements 220a-220f, as illustrated in FIG. 4. For example, it is envisioned that the multiplexer 260 may be configured to regulate the current in any fashion by switching "on" and "off" various amounts of the plurality of conductive elements 220a-220f. While the multiplexer 260 is illustrated between the generator 120 and the connection device 300, other locations for the multiplexer 260 are envisioned and within the scope of the present disclosure.

The present disclosure also includes a method for performing monopolar surgery. The method utilizes one or more return pads operatively associated to one another which form a current detection system 400 as described above. The method also includes placing one or more return pads of the current detection system 400 in contact with a patient; generating electrosurgical energy via an electrosurgical generator 120; supplying the electrosurgical energy to the patient via a surgical instrument 110; measuring the current returning to each conductive pad 210a-210d; detecting imbalances in current by comparing the current returning to one conductive pad 210a with the current returning to each of the remaining pads 210b-210d; warning the user of possible hazardous conditions; and providing a means for substantially correcting the imbalances.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. For example, it is envisioned for the return electrode 200 to be at least partially coated with a positive temperature coefficient (PTC) material to help distribute the heat across the return electrode 200, as described in commonly-owned U.S. Provisional Patent Application Ser. No. 60/666,798, the entire contents of which are hereby incorporated by reference herein.

What is claimed is:

1. A return pad current detection system for use in monopolar surgery, comprising:
   a plurality of conductive pads, wherein each conductive pad includes a plurality of conductive elements;
   a plurality of sensors operatively connected to the plurality of conductive pads which sense current returning to each pad; and
   a comparator which determines the difference in current among the plurality of conductive pads, said comparator operatively connected to a warning device which warns a user if the current differential among pads is above or below a certain predetermined limit,
   wherein the comparator receives an output of at least two distinct AC to DC converters that are in operative electrical communication with the plurality of sensors.

2. The return pad current detection system according to claim 1, further comprising an ablation generator, wherein the ablation generator regulates the amount of power delivered to a surgical device based upon the current sensed from each pad.

3. The return pad current detection system according to claim 2, wherein the ablation generator utilizes information provided by at least one comparator to substantially correct a current differential among pads.

4. The return pad current detection system according to claim 3, wherein the information provided to the ablation generator is processed by neural networks or fuzzy logic algorithms.

5. The return pad current detection system according to claim 1, wherein the sensor is a current sense transformer.

6. The return pad current detection system according to claim 1, wherein the sensor is a non-inductive sense resistor.

7. The return pad current detection system according to claim 1, wherein the comparator is a differential or instrumentation amplifier.

8. The return pad current detection system according to claim 1, wherein the sensor is a Hall-Effect device.

9. The return pad current detection system according to claim 1, further comprising a full-wave rectifier connected to the plurality all of sensors, wherein the full-wave rectifier substantially converts a signal from AC to DC.

10. A method for performing monopolar surgery, the method comprising the steps of:
    providing a return pad current detection system comprising:
      a plurality of conductive pads, wherein each conductive pad includes a plurality of conductive elements, the conductive pad defining a perimeter;
      a plurality of sensors operatively connected to the plurality of conductive pads which sense current returning to each pad; and
      a comparator which determines the difference in current among the plurality of conductive pads, wherein the comparator receives an output of at least two distinct AC to DC converters that are in operative electrical communication with the plurality of sensors;
    placing the return pad current detection system in contact with a patient;
    generating electrosurgical energy via an electrosurgical generator;
    supplying the electrosurgical energy to the patient via an active electrode;
    measuring, with the plurality of sensors, the current returning to each conductive pad;
    detecting with the comparator, imbalances in current by comparing the current returning to one conductive pad with the current returning to each of the remaining pads;
    warning the user of possible hazardous conditions; and
    regulating the imbalances among pads.

11. The method for performing monopolar surgery according to claim 10, wherein the current returning to each conductive pad undergoes full-wave rectification resulting in direct current.

12. The method for performing monopolar surgery according to claim 10, further comprising the step of curing the imbalances using one or more safety control algorithms.

13. The method for performing monopolar surgery according to claim 12, wherein the safety control algorithms are operatively associated with an ablation generator.

14. The method for performing monopolar surgery according to claim 10, wherein the current returning to each conductive pad is measured using at least one of a current-sense transformer and a non-inductive sense resistor.

15. The method for performing monopolar surgery according to claim 10, wherein the imbalances in current are detected using a series of differential or instrumentation amplifiers.

16. A return pad current detection system for use in monopolar surgery, comprising;
    an electrosurgical generator capable of generating electrical current;
    a plurality of conductive pads, wherein each conductive pad includes a plurality of conductive elements, the conductive pad defining a perimeter;
    a plurality of sensors operatively connected to the plurality of conductive pads which sense current returning to each pad;
    a plurality of ac to dc converters producing an output, wherein each converter is connected to a respective sensor of each pad; and
    a plurality of differential sensing devices, wherein each sensing device receives the output of at least two distinct ac to dc converters and each sensing device's output corresponds to a signal representative of the current differential among at least two pads.

17. A return pad current detection system according to claim 16, wherein the electrosurgical generator provides a warning if the current differential among pads is above or below a certain limit.

18. The return pad current detection system according to claim 16, wherein the electrosurgical generator modulates the amount of power delivered if the current differential among pads is above or below a certain limit.

19. The return pad current detection system according to claim 16, wherein the sensor is at least one of a current-sense transformer and non-inductive sense resistor.

20. The return pad current detection system according to claim 16, wherein the differential sensing device is at least one of a differential amplifier and an instrumentation amplifier.

21. The return pad current detection system according to claim 16, wherein the ac to dc converter is a full-wave rectifier.

* * * * *